United States Patent
Hofstraat et al.

(10) Patent No.: US 6,818,453 B1
(45) Date of Patent: Nov. 16, 2004

(54) LABEL FOR MAKING A CHARGE-TRANSFER FLUORESCENT PROBE

(75) Inventors: Johannes W. Hofstraat, Doetinchem (NL); Jan W. Verhoeven, Koog aan de Zaan (NL); Marijn Goes, Amsterdam (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 221 days.

(21) Appl. No.: 09/463,277

(22) PCT Filed: May 21, 1999

(86) PCT No.: PCT/EP99/03586

§ 371 (c)(1),
(2), (4) Date: Jan. 26, 2000

(87) PCT Pub. No.: WO99/61917

PCT Pub. Date: Dec. 2, 1999

(30) Foreign Application Priority Data

May 26, 1998 (EP) .............................................. 98201730

(51) Int. Cl.[7] .............................................. G01N 21/64
(52) U.S. Cl. ...................................................... 436/172
(58) Field of Search ......................................... 436/172

(56) References Cited

PUBLICATIONS

Krijnen B. et al. "Effect of Through–Bod Interaction on Conformation and Structure of Some N–Arylpiperidone and N–Aryltropanone Derivatives" J. Am. Chem. Soc. (1989) vol. 111, pp. 4433–4440.*

Goes M. et al. "A Blue Excitable Charge–Transfer Fluroescent Probe and Its Fluorogenic Derivative" Eur. J. Org. Chem. (1998) pp. 2373–2377.*

Verhey H.J. et al "A Fluorogenic Charge–Transfer Polarity Probe for the Derivatization of Thiols and Amines" New Journal of Chemistry, (1996) vol. 20, pp. 809–814.*

* cited by examiner

Primary Examiner—Jeffrey Snay
(74) Attorney, Agent, or Firm—Ernestine C. Bartlett

(57) ABSTRACT

The invention pertains to a non-fluorescent label which is suitable for making a charge-transfer fluorescent probe having a donor-bridge-acceptor structure, characterized in that the label comprises a maleimide moiety and the donor-bridge-acceptor structure, wherein the bridge is a group which leads to an all-trans orbital coupling of the donor and the acceptor, and the donor-bridge-acceptor structure has a higher energy charge-transfer emissive state than at least one non-emissive state of part of the label comprising the maleimide moiety, which non-emissive state must have a higher energy than the charge-transfer emissive state of the donor-bridge-acceptor structure after coupling of the maleimide moiety to a suitable system.

(I)

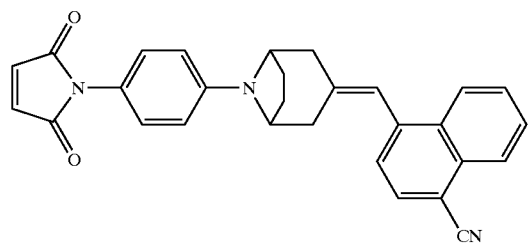

6 Claims, No Drawings

LABEL FOR MAKING A CHARGE-TRANSFER FLUORESCENT PROBE

The invention pertains to a label which is suitable for making a charge-transfer fluorescent probe, to a charge-transfer fluorescent probe comprising said label, to a diagnostic kit comprising the same, and to a method for detecting a material by using said charge-transfer fluorescent probe.

Donor-bridge-acceptor systems like the interesting fluorescent molecule Fluoroprobe (FP) have already been studied extensively (see, for instance, R. M. Hermant, N. A. C. Bakker, T. Scherer, B. Krijnen, and J. W. Verhoeven, *J.Am.Chem.Soc.* 112 (1990) 1214–1221) and used as fluorescent probes (inter alia, J. W. Hofstraat, H. J. Verhey, J. W. Verhoeven, M. U. Kumke, G. Li, S. L. Hemmingsen, and L. B. McGown, *Polymer* 38 (1997) 2899–2906). Fluoroprobe shows a characteristic intramolecular charge transfer fluorescence that depends strongly on the polarity and polarizability of the medium; the fluorescence maximum shifts from 407 nm in a non-polar environment, like n-hexane, to 697 nm in polar acetonitrile. The main disadvantage of the Fluoroprobe system lies in its poor absorption characteristics. Fluoroprobe has no significant absorption above 350 nm, which strongly reduces its applicability in (bio)polymer experiments.

It has now been found that these problems can be solved by using a label which is suitable for making a charge-transfer fluorescent probe having a donor-bridge-acceptor structure and a maleimide moiety. These labels exhibit enhanced through-bond interaction between the donor and the acceptor.

The invention therefore relates to a non-fluorescent label which is suitable for making a charge-transfer fluorescent probe having a donor-bridge-acceptor structure, characterized in that the label comprises a maleimide moiety and the donor-bridge-acceptor structure, wherein the bridge is a group which leads to an all-trans orbital coupling of the donor and the acceptor, and the donor-bridge-acceptor structure has a higher energy charge-transfer emissive state than at least one non-emissive state of part of the label comprising the maleimide moiety, which non-emissive state must have a higher energy than the charge-transfer emissive state of the donor-bridge-acceptor structure after coupling of the maleimide moiety to a suitable system.

The maleimide moiety can be any maleimide group which may optionally be substituted or wherein one or both oxygen atoms may be replaced by sulfur. The maleimide moiety can be coupled to a system to obtain a fluorescent probe, preferably a (bio)macromolecular system. Such a system comprises a group which is able to couple to the maleimide moiety, such as a primary or secondary amine, a thiol group, a negatively charged oxygen atom, or an activated oxygen atom having a leaving group attached thereto, a (meth)acrylate, vinyl ether, styrene, or a compound with a diene moiety which is able to react with the maleimide moiety in a Diels-Alder reaction. The maleimide moiety preferably is the unsubstituted N-maleimidoyl group.

Preferably, the acceptor moiety is an unsaturated or aromatic moiety having an electron-withdrawing group. Electron-withdrawing groups are known in the art and comprise, inter alia, nitrile, nitro, carbonyl, and halogen groups. Suitable aromatic groups are phenyl, naphthyl, furanyl, and thienyl groups, which may be substituted or may contain hetero atoms (for phenyl and naphthyl groups). If unsaturated moieties contain more than one unsaturated bond, these bonds are conjugated bonds.

The donor moiety comprises an aromatic moiety with an electron-donating group. The aromatic moiety is, preferably, phenyl or naphthyl, whereas the electron-donating group is a nitrogen, oxygen, sulfur, or phosphorous atom. Preferably the electron donating group is a nitrogen atom. This atom is directly attached to the aromatic moiety. When the electron-donating moiety is a nitrogen atom, the nitrogen atom of the maleimide moiety may be the electron-donating group.

The bridge moiety enables the transfer of charge from the donor moiety to the acceptor moiety. This bridge moiety is a group which leads to an all-trans orbital coupling of the donor and the acceptor. Examples are conjugated unsaturated groups and groups without conjugated unsaturated bonds but with a configuration which leads to the all-trans orbital coupling of orbitals of the donor with orbitals of the acceptor. Such groups lead to a fixed axial orientation between the donor and the acceptor.

A specifically useful label has the formula:

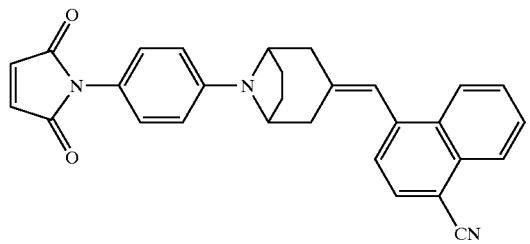

The label of this invention can be coupled to systems comprising nitrogen, sulfur or oxygen atoms, or unsaturated bonds which are able to react with the maleimide moiety. Particularly, (bio)macromolecular systems to obtain a charge-transfer fluorescent probe are useful. Such a probe can be used in diagnostic kits.

The invention further comprises a method for detecting a material by using the above-mentioned charge-transfer fluorescent probe. Excitation of such probes is performed in the 350–850 nm, more preferably in the 365–650 nm, range. Fluorescence is measured in the 370–1100 nm range.

The invention is further illustrated by the following examples.

Electronic Absorption and Fluorescence Measurements

Electronic absorption spectra were recorded on a Varian Cary 3E spectrophotometer. The samples were contained in 1 cm rectangular quartz cuvettes.

Fluorescence spectra and quantum yields were measured on a Spex Fluorolog 2 spectrofluorimeter in a right angle geometry. The spectra were corrected for the detector response. Samples were diluted to A (1 cm)≦0.2 at 308 nm.

Ethylene ketal of 8-azabicyclo[3.2.1]octan-3-one formic acid 15.9 g (73.8 mmoles) of N-benzyltropanone (Aldrich) were refluxed with 4.6 g (74 mmoles) of ethanediol and 15.1 g (79.4 mmoles) of p-toluenesulfonic acid (TsOH) in 200 ml of toluene using a Dean-Stark apparatus. After 5 h of azeotropic distillation the mixture was cooled and washed with 200 ml of 5% aq. sodium hydrogen carbonate. Infrared spectroscopy (IR) showed disappearance of the carbonyl absorption, indicating a transformation of the ketone. The organic layers were dried over sodium sulfate and evaporated. This yielded 13.4 g (52 mmoles, 70%) of the ethylene ketal of N-benzyltropanone.

11.8 g (45.5 mmoles) of the ethylene ketal of N-benzyltropanone were dissolved in 200 ml of ethanol and brought under 50 psi (344.5 kPa) hydrogen in the Parr-apparatus after addition of 75 mg of Pd/C and 2 ml of formic acid. After 80 h the catalyst was filtered off and the solvent was evaporated. After another 60 h with new catalyst $^1$H-NMR showed almost complete disappearance of the benzyl group. Yield: 7.9 g of a colorless solid (39.3 mmoles, 86%).

p-Nitro-N-phenyl-8-azabicyclo[3.2.1]octan-3-one 6.8 g (33.8 mmoles) of the above-mentioned colorless solid were dissolved in 100 ml of N,N-dimethylformamide (DMF). Under an atmosphere of nitrogen 7.0 g (50 mmoles) of potassium carbonate were added. Then 4.77 g (33.8 mmoles) of p-fluoronitrobenzene in 20 ml of DMF were added. The reaction mixture was stirred during 24 h at 100° C. and poured into 400 ml of 0.1M sodium hydroxide. The aqueous solution was extracted with ethyl acetate. The organic layers were combined, washed with water, and dried on sodium sulfate. Evaporation yielded an oil, which was dissolved in dichloromethane, washed with water, dried on sodium sulfate, and evaporated to dryness. 10.2 g of a yellow/brown solid were obtained, which were purified on a column of silica with dichloromethane as eluent, yielding 5.7 g (19.7 mmoles, 58%) of the ketal of p-nitrophenyltropanone.

This ketal of p-nitrophenyltropanone (5.7 g) was dissolved in 400 ml of 4M hydrochloric acid and the mixture was stirred overnight. The solution was made alkaline (pH 8–9) with sodium hydrogencarbonate and sodium hydroxide and extracted with dichloromethane. The organic layers were collected, dried over sodium sulfate, and evaporated to yield 4.16 g (17 mmoles, 87%) of a yellow tropanone.

p-Nitro-N-phenyl-3-[(4-cyano-1-naphthyl)methyl]-8-azabicyclo[3.2.1]octane 2.43 g (10 mmoles) of the tropanone and 3.02 g (10 mmoles) of diethyl 4-cyano-1-naphthalene methane phosphonate were dissolved in 150 ml of dry tetrahydrofuran. The solution was brought under nitrogen and 1.1 g of sodium hydride (55–60% dispersion in oil) were added slowly. The reaction mixture was stirred overnight, then 200 mg of additional sodium hydride were added, and the mixture was left to stir for 5 h more. The mixture was poured into 250 ml of water and extracted with dichloromethane The organic layers were collected, dried over sodium sulfate, and evaporated to dryness. The product was separated by flash column chromatography (silica, dichloromethane) to yield 2.2 g (5.6 mmoles, 56.5%) of fine yellow flakes.

p-(N-maleimido)-N-phenyl-3-[(4-cyano-1-naphthyl) methyl]-8-azabicyclo[3.2.1]-octane (MFT)

1.4 g (3.5 mmoles) of the fine yellow flakes as obtained above were dissolved in 200 ml of ethanol (dried on mol. sieves). Under nitrogen 4.6 g (20.3 mmoles) of tin(II) chloride dihydrate were added. The temperature was raised to 60° C. and a solution of 130 mg of sodium borohydride in 100 ml of ethanol was slowly added. The mixture was allowed to stir for 48 h, after which the solution was made alkaline (pH 8) and extracted with dichloromethane. The organic layers were dried on sodium sulfate and evaporated to dryness. Recrystallization from ethanol yielded 0.95 g (2.6 mmoles, 74%) of p-amino-N-phenyl-3-[(4-cyano-1-naphthyl)methyl]-8-azabicyclo[3.2.1]octane (the aminofluorotrope).

466 mg (3.05 mmoles) of N-methoxycarbonyl maleimide were dissolved in 50 ml dry DMF and brought under a nitrogen atmosphere. The temperature was raised to 70° C. and a solution of 550 mg (1.52 mmoles) of the aminofluorotrope in 50 ml of dry DMF was added dropwise. The temperature was raised to 120° C. and the mixture was stirred overnight. The DMF was removed in vacuo and the product (MFT) was purified over a silica column (flash chromatography) with dichloromethane as eluent and subsequently over a silica column with ethyl acetate.

n-butylamine-MFT adduct

Electronic spectra of FT and MFT show an increase in absorption in the long wavelength region with a charge-transfer band estimated to be $\epsilon \approx 4700$ M$^{-1}$cm$^{-1}$ at 350 nm. In sharp contrast to the strongly fluorescent nature of FT, its maleimide derivative MFT is completely non-fluorescent in all solvents investigated.

Equimolar amounts of MFT and n-butylamine were dissolved in dichloromethane. The mixture was heated at 40° C. overnight. The solvent was evaporated in vacuo and the product (n-butyl-MFT) was used for measurements without further purification.

TABLE

CT Fluorescence maximums ($\sigma_{CT}$ in $10^3$ cm$^{-1}$) of the MFT/n-butylamine adduct of the invention in various solvents

| Solvent | n-butyl-MFT | $\sigma_{ct}$ FT | MFT |
|---|---|---|---|
| cyclohexane | 23.8 | 23.7 | —[1)] |
| toluene | 21.1 | 20.8 | — |
| diethyl ether | 19.9 | 19.7 | — |
| ethyl acetate | 17.9 | 17.6 | — |
| dichloromethane | 17.4 | 17.1 | — |

[1)]no fluorescence at any wavelength

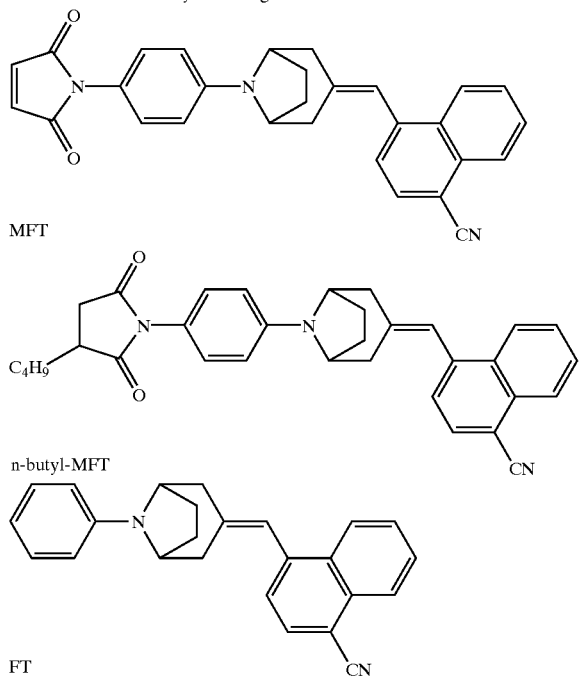

MFT n-butyl-MFT

FT

The resulting n-butyl-MFT adduct displays charge-transfer fluorescence at a position quite similar to FT (a minor blue shift occcurs, see Table) thus demonstrating that MFT can be employed as a fluorogenic label.

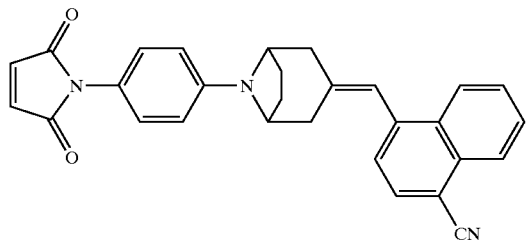

What is claimed is:

1. A non-fluorescent label which is suitable for making a charge-transfer fluorescent probe having a donor-bridge-acceptor structure, characterized in that the label comprises a maleimide moiety and a donor-bridge-acceptor structure, wherein the bridge is an 8-azabicyclo[3,2,1]octane comprising group which leads to an all-trans orbital coupling of the donor and the acceptor, and the donor-bridge-acceptor structure has a higher energy charge-transfer emissive state than at least one non-emissive state of the part of the label comprising the maleimide moiety, which non-emissive state must have a higher energy than the charge-transfer emissive state of the donor-bridge-acceptor structure after coupling of the maleimide moiety to a suitable system.

2. The label of claim 1 wherein the malemide moiety is an unsubstituted N-maleimidoyl group.

3. The label of claim 1 wherein the acceptor moiety is an unsaturated or aromatic moiety having an electron withdrawing group.

4. The label of claim 1 wherein the donor moiety comprises an aromatic moiety with an electron donating group.

5. The label of claim 4 wherein the electron donating group is the nitrogen atom of the maleimide moiety or another nitrogen which is bonded to the aromatic moiety of the donor moiety.

6. The label of claim 1 having the formula: